United States Patent
Strauch, III et al.

(10) Patent No.: US 7,567,391 B1
(45) Date of Patent: Jul. 28, 2009

(54) RADIATION SOURCE WITH SELF-ALIGNING OPTICS

(75) Inventors: Lester D. Strauch, III, Bel Air, MD (US); Richard J. Kreis, Bel Air, MD (US); Russell Chipman, Tucson, AZ (US); Karlton Crabtree, Tucson, AZ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 89 days.

(21) Appl. No.: 11/748,817

(22) Filed: May 15, 2007

(51) Int. Cl.
*G02B 15/14* (2006.01)
*G02B 7/02* (2006.01)
*G02B 17/00* (2006.01)

(52) U.S. Cl. ...................... 359/703; 359/811

(58) Field of Classification Search ............... 359/726, 359/738, 739, 703, 710, 811, 822, 827; 250/461.1, 250/461.2, 372, 374, 375
See application file for complete search history.

(56) References Cited

U.S. PATENT DOCUMENTS

| | | | |
|---|---|---|---|
| H1843 H * | 3/2000 | Bur et al. ............... | 250/461.1 |
| 2004/0130807 A1 * | 7/2004 | Hattori et al. ........... | 359/811 |
| 2005/0264900 A1 * | 12/2005 | Ishida et al. ............ | 359/811 |

* cited by examiner

*Primary Examiner*—Alicia M Harrington
(74) *Attorney, Agent, or Firm*—Ulysses John Biffoni

(57) ABSTRACT

A radiation source has a radiation-emitter assembly disposed, at least in part, in a first compartment of a housing. A lens system is disposed in a second compartment of the housing so that the lens system is optically coupled to the radiation-emitter assembly. A mirror is disposed in a third compartment of the housing so that the mirror is optically coupled to the lens system. A filter and a conduit are disposed in a fourth compartment of the housing so that the filter and an aperture provided by the conduit are optically coupled to the mirror. Radiation exits the radiation source through the aperture.

23 Claims, 10 Drawing Sheets

US 7,567,391 B1

RADIATION SOURCE WITH SELF-ALIGNING OPTICS

GOVERNMENT INTEREST

The invention described herein may be manufactured, licensed, and used by or for the U.S. Government.

TECHNICAL FIELD

The present invention relates to radiation sources.

BACKGROUND

Many particle detectors for detecting biological agent aerosols, e.g., the Tier-3 Biological Aerosol Warning System, are based on the fact that biological materials fluoresce when irradiated with ultraviolet radiation (or light). Some conventional detectors have an optical cavity that defines a focal point within the optical cavity. The biological agent aerosol is directed at the focal point along with the ultraviolet light from an ultraviolet radiation (or light) emitter, such as a laser or an LED, and the ultraviolet light generates fluorescence from the biological agent aerosol at or near the focal point. However, problems can occur when using light emitters, e.g., semiconductor ultraviolet optical sources (SUVOSs), that have both a primary emission band with a center wavelength in the ultraviolet region (i.e., a primary emission band that is capable of eliciting a fluorescence response from a biological aerosol) and a secondary emission at longer wavelengths that overlaps and interferes with the fluorescence response. In particular, the secondary emission band can be scattered by particles in the aerosol detector's optical cavity, thereby creating a positive response signal in the aerosol detector regardless of whether the scattering particle was a biological molecule or not.

Filtering optics are sometimes located between the SUVOS and the focal point to attenuate radiation that is emitted in the secondary emission band. However, such filtering optics can make the distance between the SUVOS and the focal point undesirably long for use in some particle detectors and thus can make these detectors undesirably large and difficult to transport. Another problem is that setting up the filtering optics is often difficult and time consuming.

SUMMARY

A radiation source has a radiation-emitter assembly disposed, at least in part, in a first compartment of a housing. A lens system is disposed in a second compartment of the housing so that the lens system is optically coupled to the radiation-emitter assembly. A mirror is disposed in a third compartment of the housing so that the mirror is optically coupled to the lens system. A filter and a conduit are disposed in a fourth compartment of the housing so that the filter and an aperture provided by the conduit are optically coupled to the mirror. Radiation exits the radiation source through the aperture.

DETAILED DESCRIPTION

In the following detailed description of the present embodiments, reference is made to the accompanying drawings that form a part hereof, and in which are shown by way of illustration specific embodiments that may be practiced. These embodiments are described in sufficient detail to enable those skilled in the art to practice disclosed subject matter, and it is to be understood that other embodiments may be utilized and that process changes may be made without departing from the scope of the claimed subject matter. The following detailed description is, therefore, not to be taken in a limiting sense, and the scope of the claimed subject matter is defined only by the appended claims and equivalents thereof.

Figure 1:
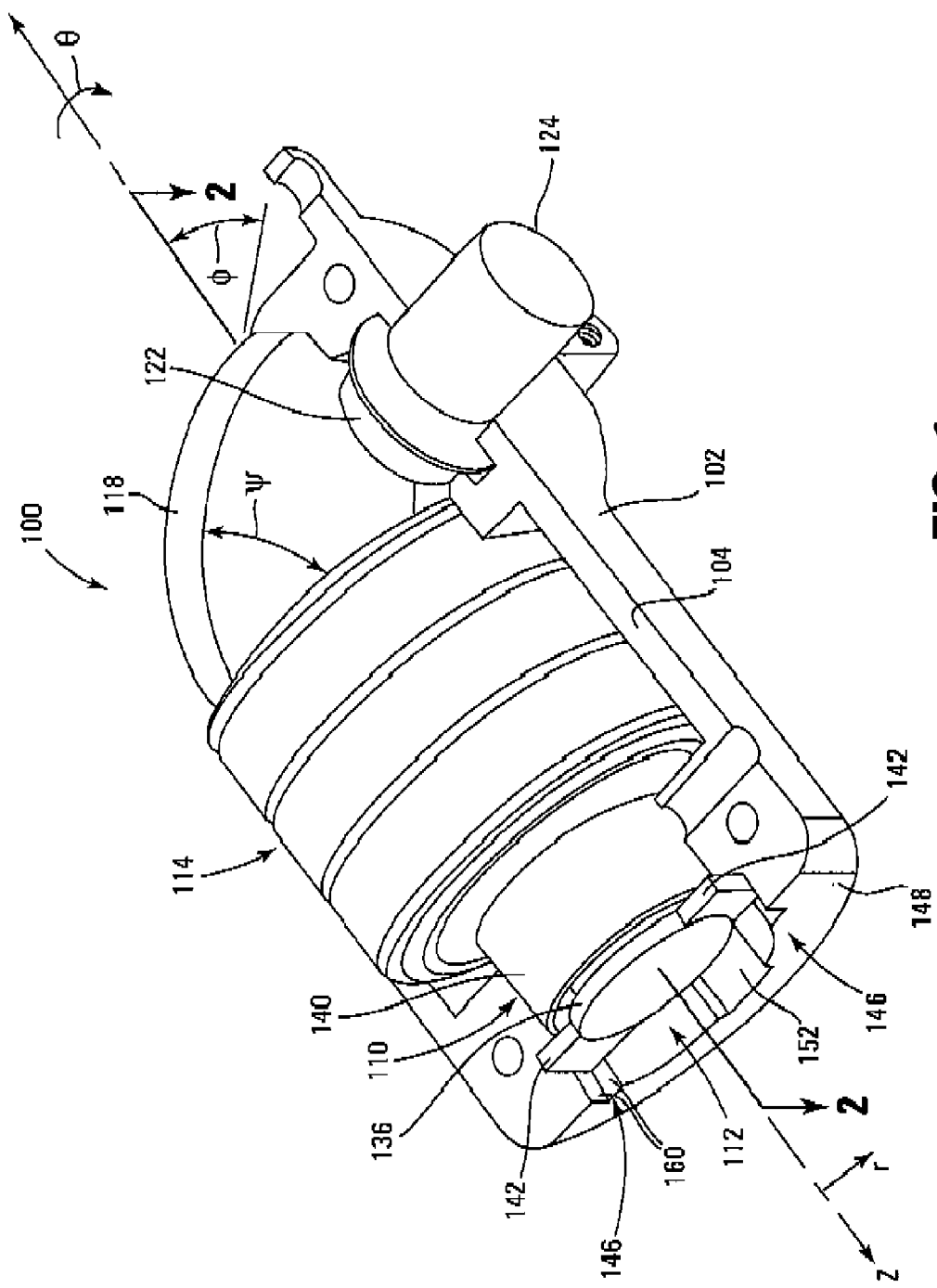
FIG. 1 is an isometric view of an embodiment of a radiation (or light) source with a portion of a housing removed, according to an embodiment of the disclosure.
Figure 2:
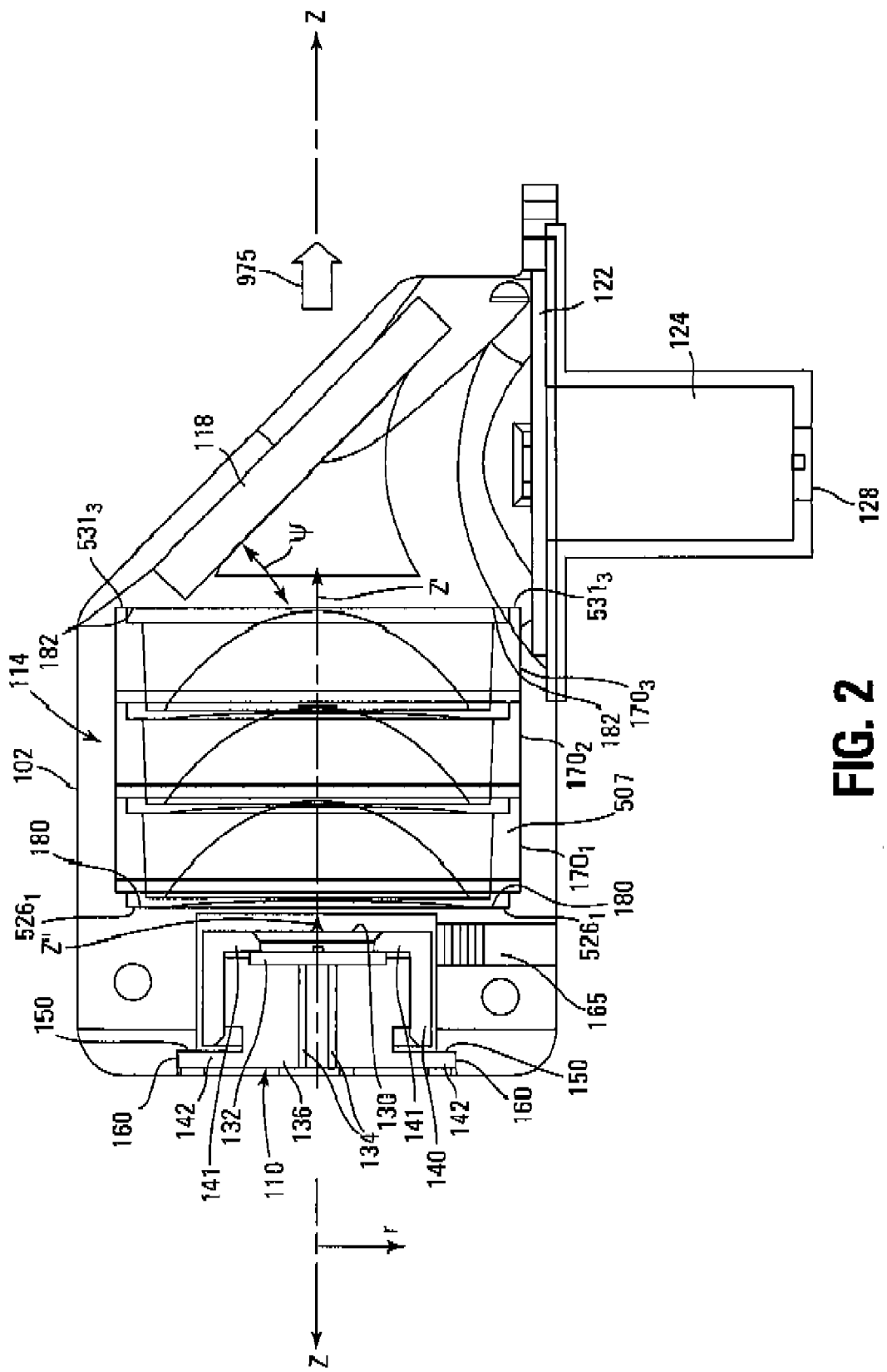
FIG. 2 is a view taken along line 2-2 of FIG. 1, according to another embodiment of the disclosure.

FIG. 1 is an isometric view of a radiation (or light) source 100 with a portion of a housing removed, according to an embodiment. FIG. 2 is a view taken along the line 2-2 of FIG. 1. Radiation source 100 is configured to provide a collimated beam of ultraviolet radiation (or light) at a focal point, such as the focal point within a shell or optical cavity of a particle detector, for producing fluorescence when a biological agent, e.g., in the form of an aerosol, is present at the focal point. For one embodiment, one or more radiation sources 100 may be used in conjunction with the particle (or biological aerosol) detectors described in U.S. Pat. No. 6,967,338 and U.S. patent application Ser. No. 11/268,758, filed Nov. 3, 2005, both of which are incorporated herein by reference in their entirety.

Figure 3:
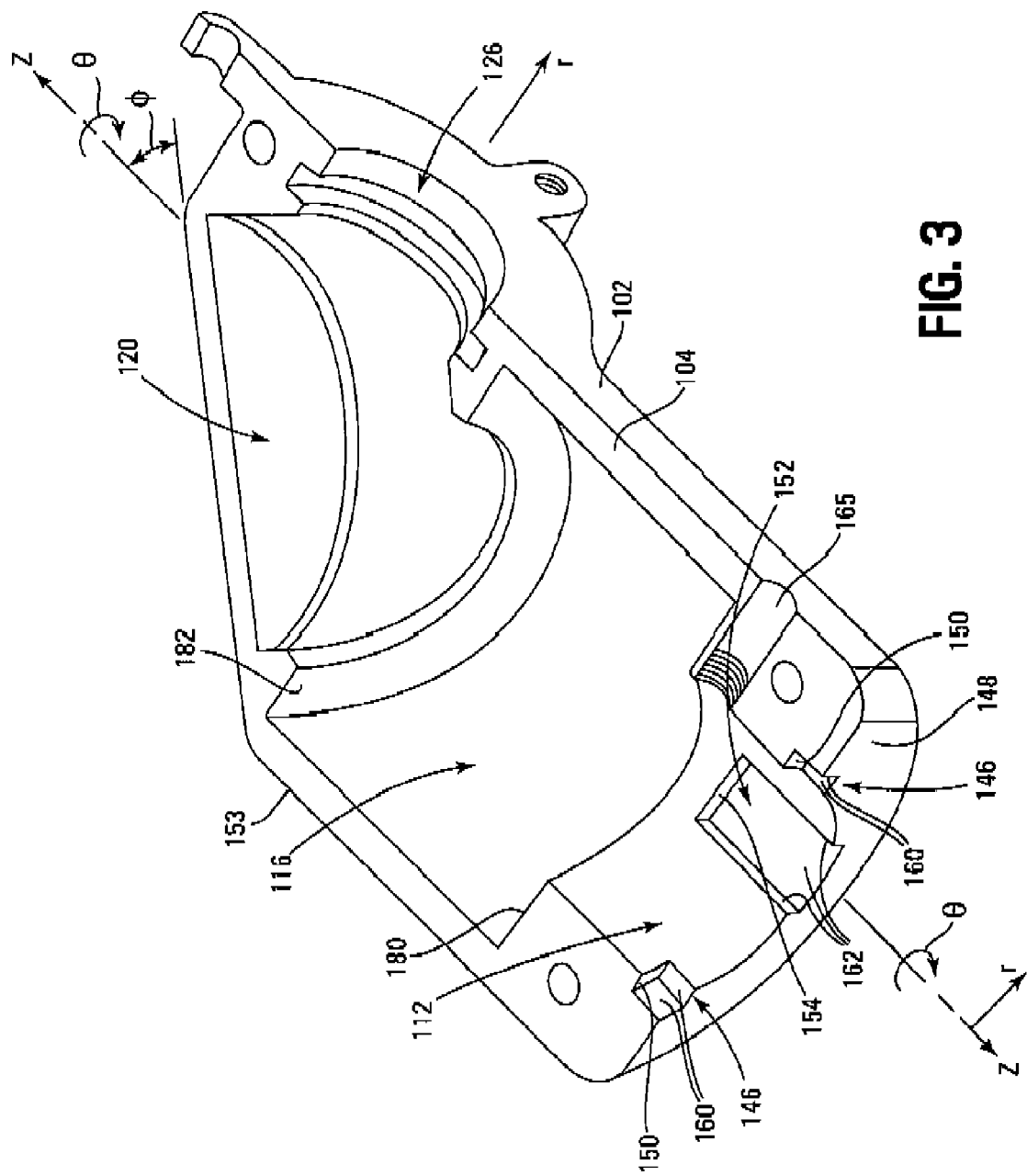
FIG. 3 is an isometric view of an interior of an embodiment of a housing of a radiation source, according to another embodiment of the disclosure.

Radiation source 100 includes a housing 102, as shown in FIGS. 1 and 2. An interior of housing 102, with its contents removed, is shown in FIG. 3. Note that a portion of housing 102 is removed in FIGS. 1 and 3. The removed portion is a minor image of the portion of housing 102 shown in FIGS. 1 and 3. The removed portion of housing 102 abuts the portion of housing 102 shown in FIGS. 1 and 3 at surface 104 so that housing 102 is symmetric about surface 104. For one embodiment, the abutted portions of housing 102 may be secured together by fasteners, such as bolts or cap screws.

Radiation source 100 also includes a radiation-emitter assembly 110 (FIGS. 1 and 2) that is disposed in a compartment 112 (FIG. 3) of housing 102. A lens system 114 is disposed a compartment 116 (FIG. 3) of housing 102. For one embodiment, lens system 114 has two or more lens elements 170 positioned one after the other in series (FIG. 2) in the axial (or longitudinal or z) direction. A mirror 118, e.g., a dichroic mirror, (FIGS. 1 and 2) is disposed in a compartment 120 (FIG. 3). A filter 122 and a conduit 124 (FIGS. 1 and 2)

are disposed in a compartment 126 (FIG. 3) of housing 102 so that conduit 124 extends from an exterior of housing 102, e.g. in a radial (or r) direction, as shown in FIGS. 1 and 2. Conduit 124 provides an aperture 128 through which radiation generated by radiation-emitter assembly 110 exits radiation source 100.

Note that for one embodiment, the portion of housing 102 that includes compartments 112 and 116 is a body of revolution about the z-axis (or the central longitudinal axis of housing 102), and the portion of housing 102 that includes compartment 126 is a body of revolution about the radial (or r) direction and is thus substantially perpendicular to the portion of housing 102 that includes compartments 112 and 116. Compartment 120 is formed between compartment 126 and compartment 116, and for one embodiment, forms an angle $\phi$, e.g., about 45 degrees, with the axial (or z) direction.

Respectively disposing radiation-emitter assembly 110, lens system 114, mirror 118, and filter 122 and conduit 124 in compartments 112, 116, 120, and 126 of housing 102 positions radiation-emitter assembly 110, lens system 114, mirror 118, and filter 122 and conduit 124 at predetermined geometric locations with respect to each other so that radiation-emitter assembly 110, lens system 114, mirror 118, and filter 122 and conduit 124 are located at predetermined distances from each other and are optically aligned with little of no additional adjustment. In other words, compartments 112, 116, 120, and 126 of housing 102 and radiation-emitter assembly 110, lens system 114, mirror 118, and filter 122 and conduit 124 are configured to position radiation-emitter assembly 110, lens system 114, mirror 118, and filter 122 and conduit 124 at predetermined distances from each other and to optically align radiation-emitter assembly 110, lens system 114, mirror 118, and filter 122 and conduit 124 with little or no additional adjustment. This acts to reduce the time required for positioning and aligning radiation-emitter assembly 110, lens system 114, mirror 118, and filter 122 and conduit 124.

For one embodiment, radiation-emitter assembly 110 includes a radiation emitter 130 attached to a substrate 132 (e.g., called a "TO-can"), e.g., of metal, as shown in FIG. 2. Electrical leads 134 are attached to radiation emitter 130 for supplying power to the radiation emitter 130. For another embodiment, substrate 132, with radiation emitter 130 disposed thereon, is disposed on a base 136 having lead-outs through which the electrical leads 134 pass, as shown in FIG. 2. For another embodiment, base 136 is disposed within a holder 140, e.g., by threading, so that substrate 132 is secured between base 136 and holder 140, as shown in FIG. 2. Holder 140 includes an extension 141 that extends radially inward away from axial walls of holder 140 and toward a central longitudinal axis z" (or the center) of radiation-emitter assembly 110 and thus toward the z-axis of housing 102, as shown in FIG. 2. Substrate 132 is secured between base 136 and extension 141 when base 136 is threaded into holder 140, as shown in FIG. 2.

Base 136 of radiation-emitter assembly 110 has radial extensions 142 that extend radially outward away from the central longitudinal axis z", as shown in FIGS. 1 and 2, for one embodiment. Extensions 142 are received in slots 146 (FIGS. 1 and 3) formed in an interior surface of a wall 153 of housing 102 within compartment 112. Slots 146 extend axially (in a direction parallel to the z-axis) into compartment 112 from an end 148 of housing 102 and terminate at ends 150 thereof within compartment 112. The ends 150 of slots 146 abut radial extensions 142 of base 136, as shown in FIGS. 1 and 2, to prevent further axial insertion of radiation-emitter assembly 110 within compartment 112. When ends 150 of slots 146 abut radial extensions 142 of base 136 of radiation-emitter assembly 110, radiation-emitter assembly 110, and thus radiation emitter 130, is at a predetermined distance from lens system 114, as shown in FIG. 2.

Slots 152, one of which is shown in FIG. 3, are also formed in wall 153 of housing 102 within compartment 112. Note that the other slot 152 is formed in the portion of housing 152 that has been removed. For one embodiment, slots 152 are formed at 90 degrees in the angular (or $\theta$) direction, along the cylindrical surface of wall 153 within compartment 112, from slots 146, as shown in FIG. 3. Slots 152 extend axially into compartment 112 from the end 148 of housing 102 and terminate at ends 154 thereof within compartment 112, as shown in FIG. 3. Note that the ends 154 of slots 152 are located at a longer axial distance from end 148 of housing 102 than the ends 150 of slots 146. In other words, the ends 154 of slots 152 are located at a shorter axial distance from compartment 116 than the ends 150 of slots 146, as shown in FIG. 3.

The radial extensions 142 of base 136 of radiation-emitter assembly 110 can also be received in slots 152, e.g., after rotating radiation-emitter assembly 110 by 90 degrees about its central longitudinal axis z" from the position shown in FIG. 1. When ends 154 of slots 152 abut radial extensions 142 of base 136, radiation-emitter assembly 110, and thus radiation emitter 130, is at a predetermined distance from lens system 114. Since the ends 154 of slots 152 are located at a longer axial distance from the end 148 of housing 102 than the ends 150 of slots 146, radiation emitter 130 is located at a longer axial distance from the end 148 of housing 102 when radial extensions 142 of base 136 abut the ends 154 of slots 152 than when radial extensions 142 of base 136 abut the ends 150 of slots 146.

Abutting the radial extensions 142 of base 136 of radiation-emitter assembly 110 at the end 150 of slot 146 and at the end 154 of slot 152 respectively sets the axial position of the radiation emitter 130 at two different predetermined locations within housing 102. As discussed below, the two different predetermined locations of radiation emitter 130 are respectively used in conjunction with two different configurations of the lens system 114. The radial extensions 142 of base 136 of radiation-emitter assembly 110 are positioned in slot 146 for an embodiment where lens system 114 includes three lens elements 170, e.g., so as to position radiation emitter 130 adjacent lens element $170_1$, as shown in FIG. 2. For one embodiment, lens system 114 includes three lens elements 170 (lens elements $170_1$-$170_3$) for a radiation emitter 130 that emits ultraviolet radiation with a nominal wavelength of about 280 nanometers.

The radial extensions 142 of base 136 of radiation-emitter assembly 110 are positioned in slots 152 for an embodiment where lens system 114 includes two lens elements 170 (e.g., lens elements $170_2$ and $170_3$) and a spacer, e.g., that replaces lens element $170_1$. In this configuration, positioning the radial extensions 142 of base 136 of radiation-emitter assembly 110 in slots 152 positions radiation-emitter assembly 110 so that radiation-emitter assembly 110 extends into compartment 116 and into the spacer so that radiation emitter 130 is adjacent lens element $170_2$. For one embodiment, lens system 114 includes two lens elements 170 for a radiation emitter 130 that emits ultraviolet radiation with a nominal wavelength of about 345 nanometers.

The radial extensions 142 of base 136 also abut sidewalls 160 of each of slots 146 (FIG. 3) when inserted in slots 146, as shown in FIGS. 1 and 2, or abut sidewalls 162 of each of slots 152 (FIG. 3) when inserted in slots 152. This sets the radial position of radiation emitter 130 relative the z-axis, i.e., positions radiation-emitter assembly 110 so that its central longitudinal axis z" is aligned with the z axis of housing 102, as shown in FIG. 2. Therefore, slots 146 or slots 152 in conjunction with the radial extensions 142 of base 136 of radiation-emitter assembly 110 act to position radiation emitter 130 at a predetermined location within housing 102 with little or no additional adjustment.

For one embodiment, a threaded hole 165 extends inward, e.g., in the radial direction, from the exterior of housing 102 and opens into compartment 112, as shown in FIG. 3. Hole 165 aligns with holder 140 of radiation-emitter assembly 110 when the radial extensions 142 of base 136 are located in slots 146 or slots 152, as shown in FIG. 2 when the radial extensions 142 of base 136 are located in slots 146. For another embodiment, a set screw (not shown) may be threaded into hole 165 so as to engage holder 140 to fix radiation-emitter assembly 110 in place.

Figure 4:
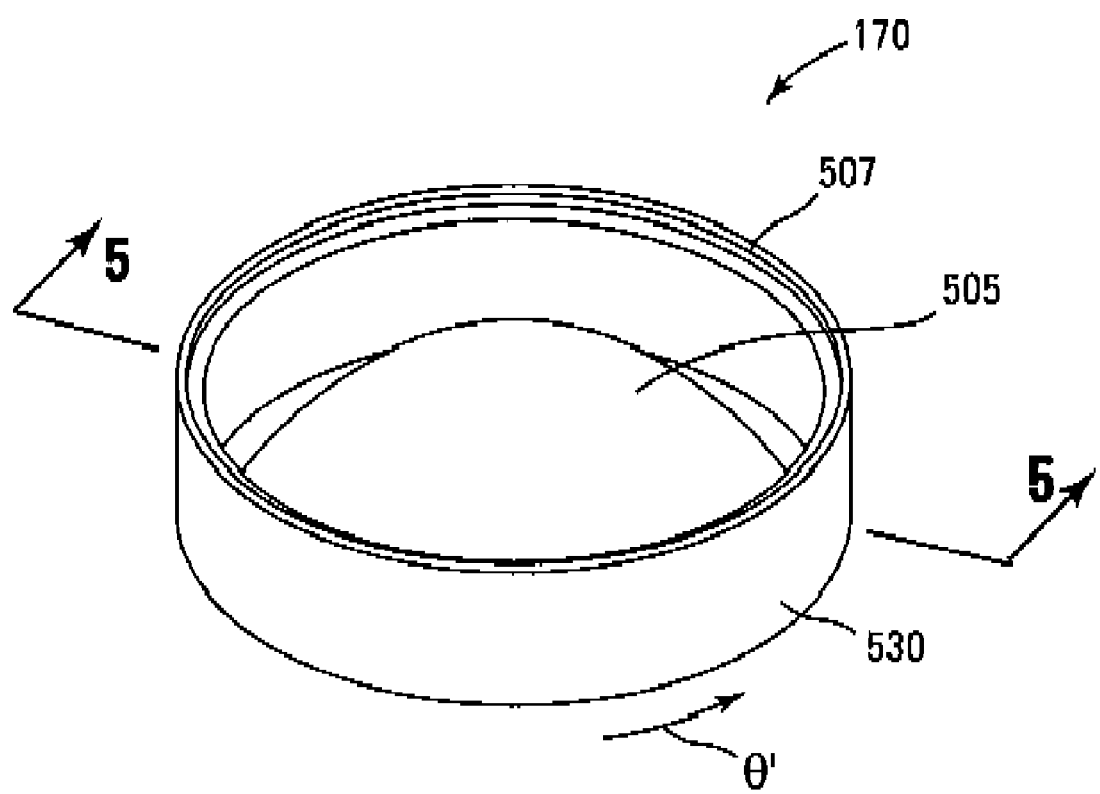
FIG. 4 illustrates an embodiment of a lens element, according to another embodiment of the disclosure.
Figure 5:
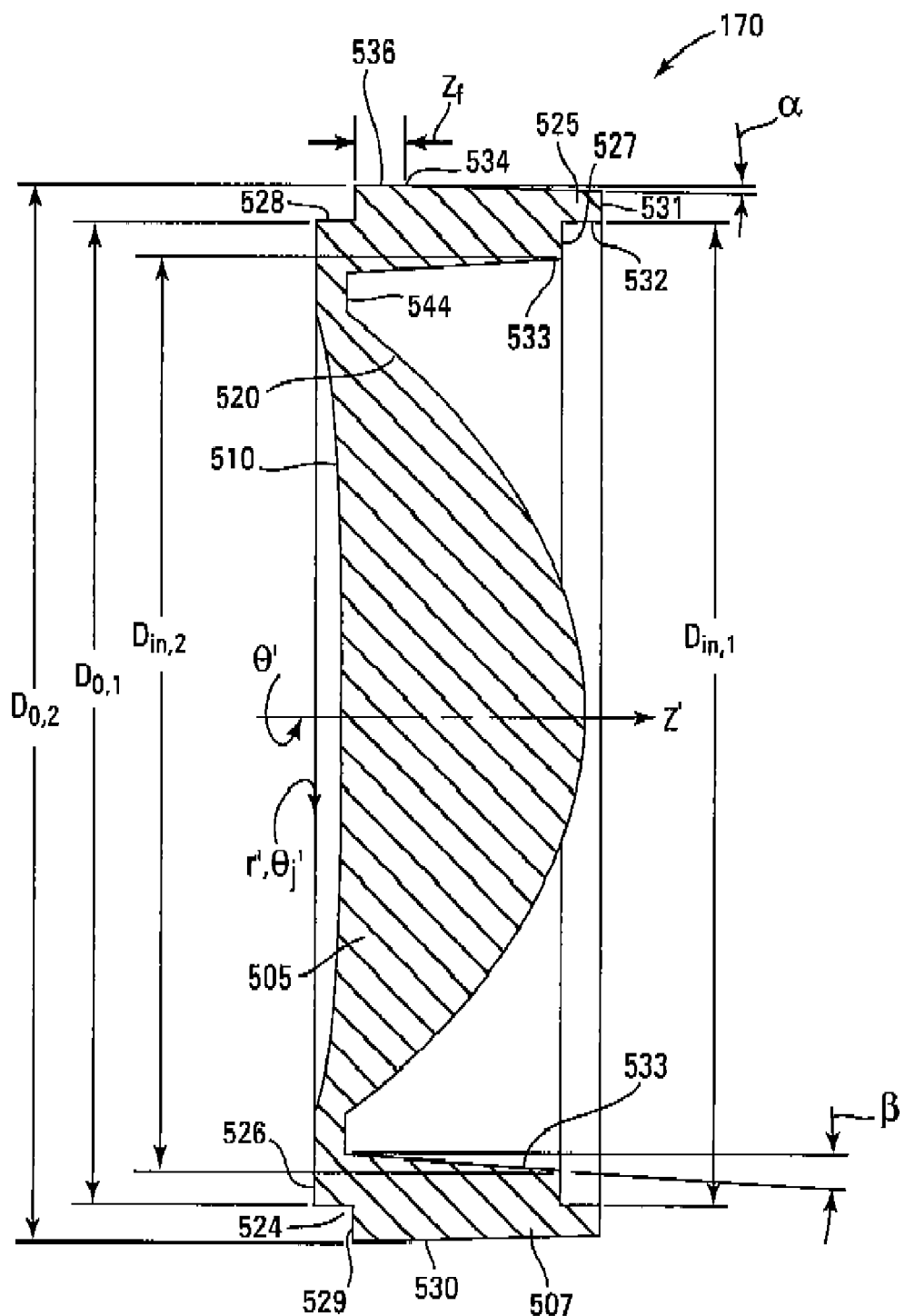
FIG. 5 is a view taken along line 5-5 of FIG. 4, according to another embodiment of the disclosure.

FIG. 4 illustrates a lens element 170, according to an embodiment. FIG. 5 is a view taken along line 5-5 of FIG. 4. Lens element 170 has a lens 505 surrounded by an integral flange 507 that extends in the axial direction away from radiation emitter 130 when installed in housing 102, as shown in FIG. 2. For one embodiment, lens element 170 is fabricated from a suitable optical plastic, such as ZEONEX or Cytop, using a one-shot injection molding process. For another embodiment, the ZEONEX is used in conjunction with a radiation emitter 130 that emits ultraviolet radiation with a nominal wavelength of about 345 nanometers, and the Cytop is used in conjunction with a radiation emitter 130 that emits ultraviolet radiation with a nominal wavelength of about 280 nanometers, because ZEONEX does not transmit ultraviolet radiation with a nominal wavelength of about 280 nanometers. Note, however, that the Cytop can also be used for ultraviolet radiation with a nominal wavelength of about 345 nanometers.

Lens 505 of lens element 170 has a surface 510 and a surface 520, as shown in FIG. 5. Surfaces 510 and 520 are surfaces of revolution obtained from rotating the two-dimensional shapes of surfaces 510 and 520 shown in FIG. 5 about a central longitudinal axis z' in an angular direction θ'. For one embodiment, radiation, e.g., generated by radiation emitter 130, enters lens 505 at surface 510 and exits lens 505 at surface 520. Note that flange 507 forms a container-shaped structure around surface 520.

For one embodiment, the two-dimensional shape of surface 510 at a fixed angular location $\theta'_j$ is completely described by a pure fourth-order curve in cylindrical coordinates (r', z') as follows:

$$z' = (-0.530668E\text{-}04)r'^4 \quad (1)$$

where z' is the axis of rotation (or central longitudinal axis) of surfaces 510 and 520 and thus of lens 505 and lens element 170. The curvature of the base sphere of surface 510 is zero.

For one embodiment, the two-dimensional shape of surface 520 at the angular location $\theta'_j$ is completely described by an ellipse E(r') in combination with a fourth-order curve as follows:

$$z' = E(r') + (0.178064E\text{-}04)r'^4 \quad (2)$$

where $$E(r') = (\text{curv})r'^2 / [1 + (1 - (1+k)(\text{curv})^2 r'^2)^{1/2}] \quad (3)$$

where curv is the curvature of the base sphere of surface 520 and is −0.09985863 and k is the conic constant and is −0.521838. Note the E(r') defines an ellipsoid of revolution when rotated about the z' axis.

For one embodiment, a notch 524 is formed in an end surface 526 of flange 507 of lens element 170, as shown in FIG. 5. For another embodiment, end surface 526 faces radiation emitter 130. An outer circumferential surface 528 of flange 507, located at an outer diameter $D_{O,1}$ of flange 507, forms a radial boundary of notch 524, as shown in FIG. 5. A radial surface 529 connected between the outer circumferential surface 528 and an outer circumferential surface 530, located at an outer diameter $D_{O,2}$ of flange 507, forms an axial boundary of notch 524, as shown in FIG. 5.

For another embodiment, an axial extension 525 extends from an end surface 527 of flange 507, where end surface 527 faces in a direction opposite to end surface 526, as shown in FIG. 5. Axial extension 525 has an end surface 531 that is substantially parallel to end surface 527 for one embodiment, that faces in substantially the same direction as end surface 527, and that is displaced axially from end surface 527 in direction away from surface 510. An inner circumferential surface 532 of flange 507, located at an inner diameter $D_{in,1}$ of flange 507, forms a radial boundary of axial extension 525, as shown in FIG. 5.

For one embodiment, outer circumferential surface 530 has a flat region 536 at the outer diameter $D_{O,2}$, as shown in FIG. 5. Flat region 536 extends over an axial distance $z_f$ from radial surface 529 to an axial location 534 on outer circumferential surface 530, as shown in FIG. 5. For another embodiment, outer circumferential surface 530 tapers inward, toward the center of lens element 170, starting at axial location 534 and ending at end surface 531 of axial extension 525. Specifically, surface 530 tapers inward, toward the center of lens element 170, at an angle α, e.g., of about one degree, from a direction parallel to the z'-axis, as shown in FIG. 5.

For one embodiment, an inner circumferential surface 533 of flange 507 tapers outward, away from the center of lens element 170, starting at a base 544 of surface 520 and ending at end surface 527, i.e., at an axial location where the inner diameter of flange 507 is $D_{in,2}$, as shown in FIG. 5. Specifically, inner circumferential surface 533 tapers outward, away from the center of lens element 170, at an angle β, e.g., of about three degrees, from a direction parallel to the z'-axis. Note that end surface 527 is connected between inner circumferential surface 533 and inner circumferential surface 532, as shown in FIG. 5.

Figure 6:
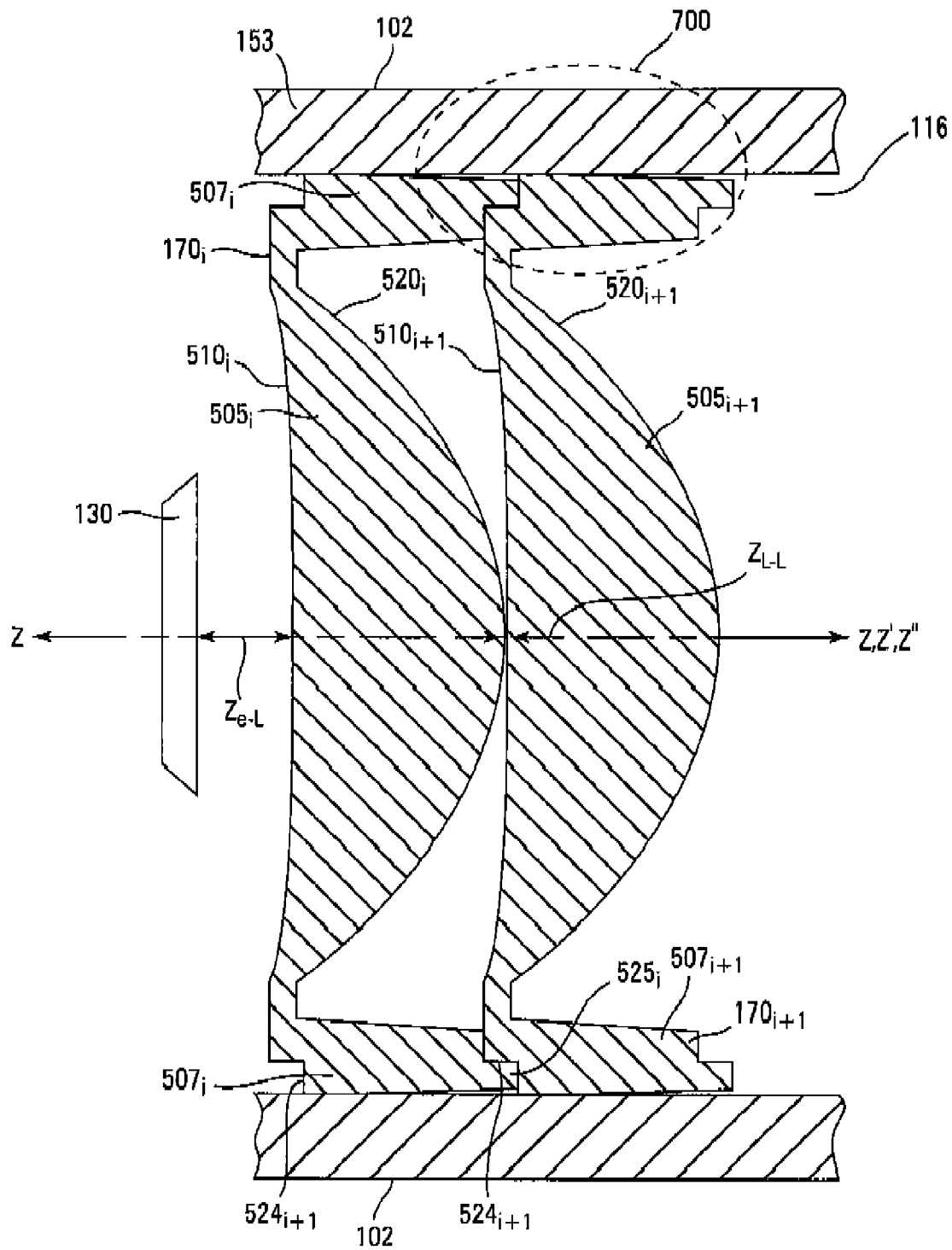
FIG. 6 is a cross-sectional view of lens elements connected in series, according to another embodiment of the disclosure.
Figure 7:
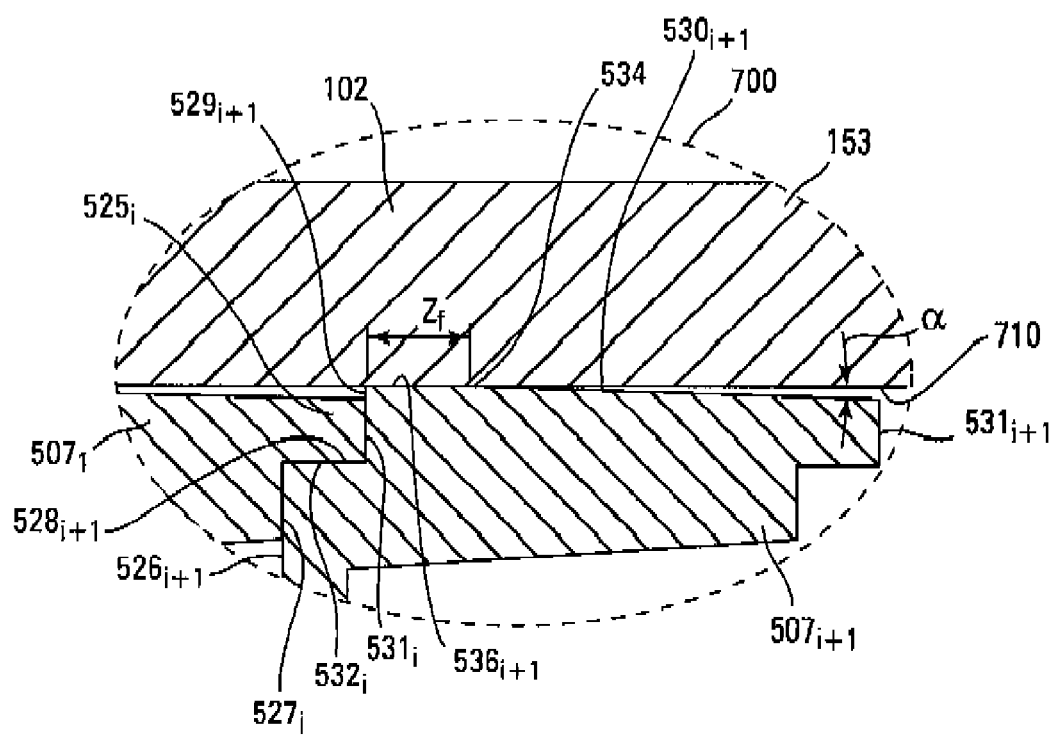
FIG. 7 is an enlarged view of a region 700 of FIG. 6, according to another embodiment of the disclosure.

FIG. 6 is a cross-sectional view of lens elements $170_i$ and $170_{i+1}$ connected in series, according to another embodiment. FIG. 7 is an enlarged view of the region 700 of FIG. 6. Receiving axial extension $525_i$ of flange $507_i$ of lens element $170_i$ in notch $524_{i+1}$ of flange $507_{i+1}$ of lens element $170_{i+1}$ connects lens elements $170_i$ and $170_{i+1}$ in series, as shown in FIG. 6.

The radial boundary of axial extension $525_i$, formed by the inner circumferential surface $532_i$ of flange $507_i$, contacts the radial boundary of notch $524_{i+1}$, formed by the outer circumferential surface $528_{i+1}$ of flange $507_{i+1}$, as shown in FIG. 7, when axial extension $525_i$ of flange $507_i$ is received in notch $524_{i+1}$ of flange $507_{i+1}$. Moreover, end surface $531_i$ of axial extension $525_i$ abuts the axial boundary of notch $524_{i+1}$, formed by radial surface $529_{i+1}$, as shown in FIG. 7, when axial extension $525_i$ of flange $507_i$ is received in notch $524_{i+1}$ of flange $507_{i+1}$. Further, end surface $527_i$ of flange $507_i$ abuts end surface $526_{i+1}$ of flange $507_{i+1}$, as shown in FIG. 7, when axial extension $525_i$ of flange $507_i$ is received in notch $524_{i+1}$ of flange $507_{i+1}$. For another embodiment, the inner diameter $D_{in,1}$ (FIG. 5) at which the inner circumferential surface $532_i$ occurs, or the outer diameter $D_{O,1}$ (FIG. 5) at which the outer circumferential surface $528_{i+1}$ occurs, or both the inner diameter $D_{in,1}$ and the outer diameter $D_{O,1}$ may be selected to produce a press fit between the inner circumferential surface $532_i$ and the outer circumferential surface $528_{i+1}$ so that inner circumferential surface $532_i$ and the outer circumferential surface $528_{i+1}$ are in forcible engagement.

For one embodiment, the flat region 536 of outer circumferential surface 530 of flange 507 of each lens element 170 (FIG. 5) contacts an interior surface of wall 153 of housing 102 within compartment 116. This is illustrated, for example, for flange $507_{i+1}$ of lens element $170_{i+1}$ in FIG. 7, where the flat region $536_{i+1}$ of outer circumferential surface $530_{i+1}$ of contacts an interior surface 710 of wall 153 of housing 102 within compartment 116. Moreover, the outer circumferential surface 530 of each lens element 170 tapers away from the interior surface of wall 153 at the angle $\alpha$ in the axial direction going away from radiation emitter 130, starting at axial location 534 and ending at end surface 531. This is illustrated, for example, for flange $507_{i+1}$ of lens element $170_{i+1}$ in FIG. 7, where the outer circumferential surface $530_{i+1}$ tapers away from the interior surface 710 of wall 153 at the angle $\alpha$, starting at axial location 534 and ending at end surface $531_{i+1}$.

As shown in FIG. 6, connecting lens elements $170_i$ and $170_{i+1}$, in series as described above, sets a predetermined axial distance $z_{L-L}$ between the vertex of surface $520_i$ of lens $505_i$ of lens element $170_i$ and the vertex of surface $510_{i+1}$ of lens $505_{i+1}$ of lens element $170_{i+1}$, with little or no additional adjustments. Connecting lens elements $170_i$ and $170_{i+1}$, also aligns lens elements $170_i$ and $170_{i+1}$ so that their central longitudinal axes of z' are aligned with each other, as shown in FIG. 6, with little or no additional adjustment.

As best shown in FIG. 3, compartment 116 is located between axial boundaries 180 and 182. When lens system 114 is disposed in compartment 116, end surface $526_1$ of lens element $170_1$ abuts axial boundary 180, and end surface $531_3$ of lens element $170_3$ abuts axial boundary 182, as shown in FIG. 2. Disposing lens system 114 in compartment 116 and disposing radiation-emitter assembly 110 in compartment 112, i.e., disposing radial extensions 142 of radiation-emitter assembly 110 in either slots 146 or 152 of compartment 112, sets the axial distance $z_{e-L}$ (FIG. 6) between radiation emitter 130 and the vertex of the surface 510 of the lens element 170 closest to radiation emitter 130, with little or no additional adjustment. Disposing lens system 114 in compartment 116 so that the flat regions 536 of the respective lens elements 170 engage the interior surface of wall 153 within compartment 116 and disposing radiation-emitter assembly 110 in compartment 112 also aligns the central longitudinal axes z of housing 102, z' of the lens elements 170 and thus lens system 114, and z" of radiation-emitter assembly 110, as shown in FIGS. 2 and 6.

Note that the subscript i in FIG. 6 is a 1 (one) when three lens elements are used (FIG. 2), and the radial extensions 142 of radiation-emitter assembly 110 are inserted into slots 146 (FIG. 1). Alternatively, the subscript i in FIG. 6 is a 2 (two) when two lens elements are used, and the radial extensions 142 of radiation-emitter assembly 110 are inserted into slots 152 (FIGS. 1 and 3).

Figure 8:
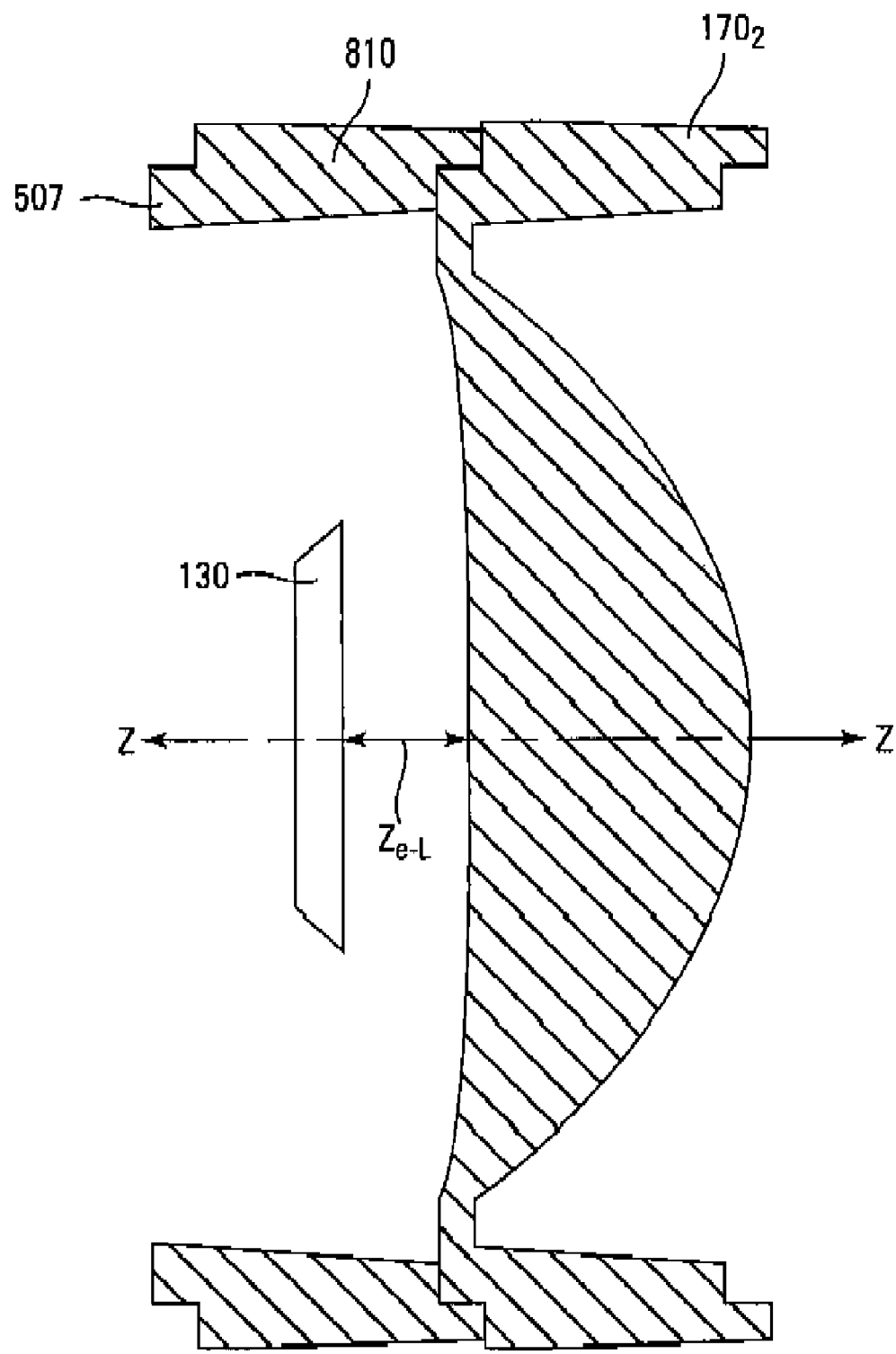
FIG. 8 is a cross-sectional view of a lens element and a spacer connected in series, according to another embodiment of the disclosure.

When two lens elements are used in conjunction with radial extensions 142 disposed in slots 152, lens element $170_1$ is replaced by a spacer 810, as shown in FIG. 8, according to another embodiment. For one embodiment, spacer 810 is a lens element 170 with the lens 505 removed and the flange 507 remaining, as shown in FIG. 8. For this embodiment, spacer 810 is connected to lens element $170_2$ in the same way as lens elements $170_i$ and $170_{i+1}$ are connected, as described above in conjunction with FIGS. 6 and 7. Note that radiation emitter 130 is located within spacer 810, which is the result of inserting the radial extensions 142 of radiation-emitter assembly 110 into slots 152. Note further that a portion of radiation-emitter assembly 110 extends from compartment 112 into compartment 116 when radial extensions 142 are disposed in slots 152 so that radiation emitter 130 is located in compartment 116.

For one embodiment, radiation emitter 130 is an ultraviolet radiation source in the form of a light-emitting diode. For another embodiment, radiation emitter 130 may be a semiconductor ultraviolet optical source (SUVOS) in the form of a light emitting diode. Semiconductor ultraviolet optical sources typically emit radiation in both primary and secondary emission bands. The primary emission band has a center wavelength in the ultraviolet region that can be used to irradiate and optically excite biological molecules in an aerosol sample. The secondary emission band has a center wavelength in the visible spectrum and is generally an unintended and unwanted companion to the primary emission band for applications involving biological molecules since its spectrum sometimes and undesirably overlaps the expected fluorescence spectrum of biological molecules excited by radiation from the primary emission band.

For another embodiment, radiation emitter 130 emits a total amount of radiation 905 over a total angle $\gamma_{tot}$, e.g., of about 178-degrees, as shown in FIG. 9, a ray diagram illustrating the operation of radiation source 100. For some embodiments, the radiation emitted by radiation emitter 130 has a numerical aperture of about 0.65 in object space. For other embodiments, emission of radiation from radiation emitter 130 is a Lambertian emission.

For one embodiment, a surface 510 of a lens 505 that is directly exposed to the radiation from radiation source 130 captures radiation 910 emitted over an angle $\gamma_0$, e.g., as shown in FIG. 9 for surface 510$_1$ of lens 505$_1$ of lens element 170$_1$. Note that in one embodiment, a surface 510 of a lens 505 may capture about 70 percent of the total amount of radiation 905 emitted from radiation emitter 130. That is, the radiation 910 emitted over the angle $\gamma_0$ in FIG. 9 is about 70 percent of the total amount of radiation 905 emitted over the total angle $\gamma_{tot}$.

In FIG. 9, the radiation 910 emitted over the angle $\gamma_0$ that is captured by surface 510$_1$ of lens 505$_1$ is contained between rays 920 and 930. Radiation 910 diverges by the angle $\gamma_0$ away from the z-axis, i.e., away from the centers of lenses 505$_1$, 505$_2$, and 505$_3$ which are coincident with the z-axis, until radiation 910 reaches surface 510$_1$ of lens 505$_1$. Radiation 910 is refracted inward toward the z-axis as it passes through surface 510$_1$ so that radiation 910 diverges by an angle $\gamma_1$, which is less than the angle $\gamma_0$, away from the z-axis between surface 510$_1$ and surface 520$_1$ of lens 505$_1$. That is, the refraction at surface 510$_1$ reduces the divergence of radiation 910 compared to the divergence before the refraction at surface 510$_1$. Radiation 910 is refracted further inward toward the z-axis as it passes through surface 520$_1$ so that radiation 910 diverges by an angle $\gamma_z$, which is less than the angle $\gamma_1$, away from the z-axis between surface 520$_1$ of lens 505$_1$ and surface 510$_2$ of lens 505$_2$. That is, the refraction at surface 520$_1$ reduces the divergence of radiation 910 compared to the divergence before the refraction at surface 520$_1$.

Radiation 910 is refracted further inward toward the z-axis as it passes through surface 510$_2$ of lens 505$_2$ so that radiation 910 diverges by an angle $\gamma_3$, which is less than the angle $\gamma_2$, away from the z-axis between surface 510$_2$ of lens 505$_2$ and surface 520$_2$ of lens 505$_2$. That is, the refraction at surface 510$_2$ reduces the divergence of radiation 910 compared to the divergence before the refraction at surface 510$_2$. Radiation 910 is refracted still further inward toward the z-axis as it passes through surface 520$_2$ so that radiation 910 diverges by an angle $\gamma_4$, which is less than the angle $\gamma_3$, away from the z-axis between surface $520_2$ of lens $505_2$ and surface $510_3$ of lens $505_3$. That is, the refraction at surface $520_2$ reduces the divergence of radiation 910 compared to the divergence before the refraction at surface $520_2$.

Radiation 910 is refracted further inward toward the z-axis as it passes through surface $510_3$ of lens $505_3$ so that radiation 910 diverges by an angle $\gamma_5$, which is less than the angle $\gamma_4$, away from the z-axis between surface $510_3$ of lens $505_3$ and surface $520_3$ of lens $505_3$. That is, the refraction at surface $510_3$ reduces the divergence of radiation 910 compared to the divergence before the refraction at surface $510_3$. Radiation 910 is refracted still further inward toward the z-axis as it passes through surface $520_3$ so that for one embodiment, radiation 910 converges by an angle $\gamma_6$, toward the z-axis between surface $520_3$ and mirror 118. That is, for one embodiment, the refraction at surface $520_3$ causes radiation 910 to transition from diverging radiation to converging radiation. The transition from diverging radiation to converging radiation need not be limited to surface $520_3$ of lens $505_3$, but could occur at other lens surfaces within lens system 114.

Mirror 118 is at the angle $\phi$ with respect to the z-axis. Note that compartment 120 which contains mirror 118 is at the angle $\phi$ and that disposing mirror 118 in compartment 120 sets the angle of mirror 118 to the angle $\phi$ with respect to the z-axis with little of no additional adjustment. Mirror 118 also forms an angle $\psi=90-\phi$ degrees with respect to the r-direction and thus lens system 114 (see FIGS. 1 and 2). Note that $\psi=\phi$ when $\phi=45$ degrees.

Figure 9:
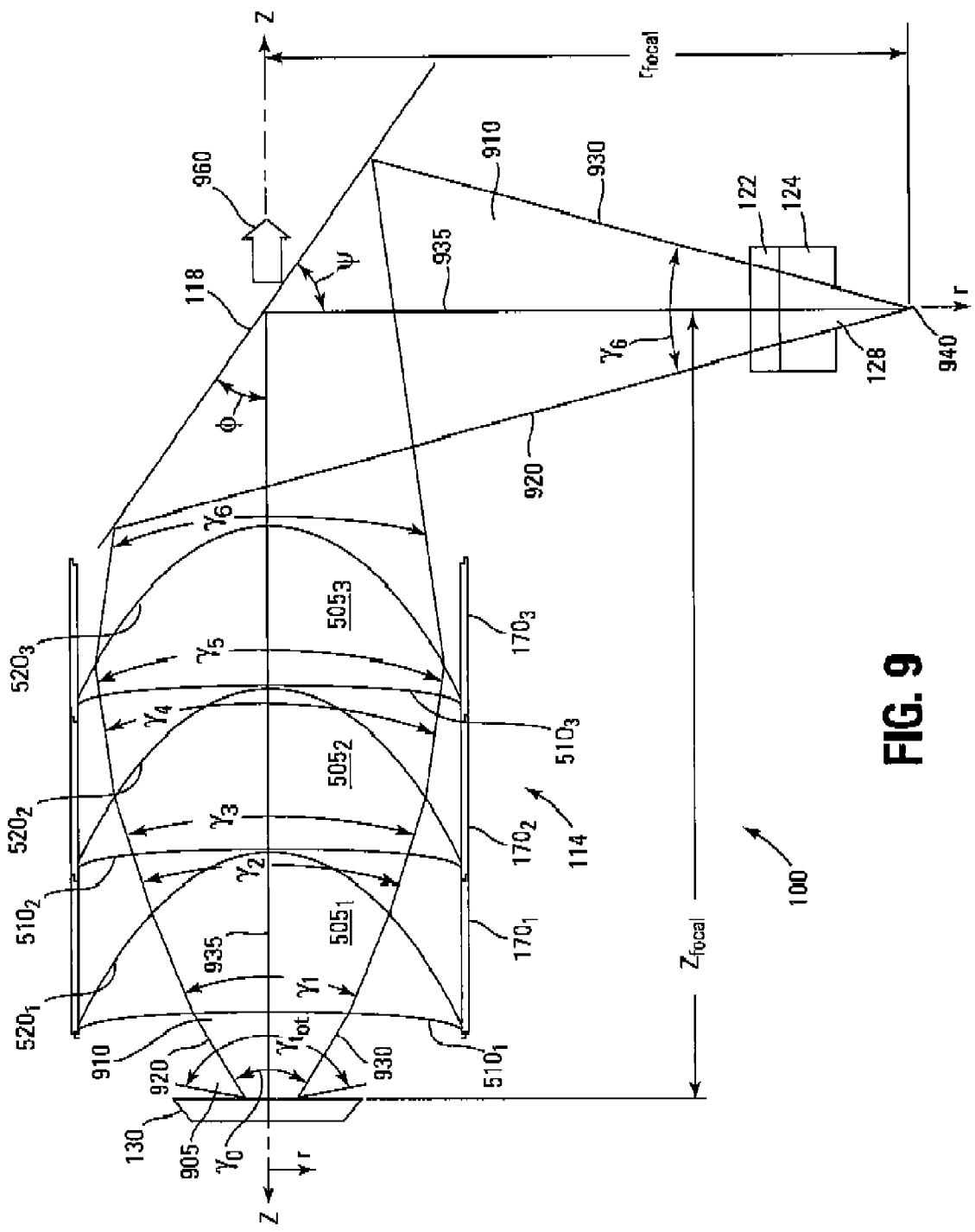
FIG. 9 is a ray diagram illustrating the operation of a radiation source, according to another embodiment of the disclosure.

The converging radiation 910 is generally axial (or generally parallel to the z-axis) when converging radiation 910 is received at mirror 118. Mirror 118 reflects the converging radiation 910 so that it is generally radial (or generally parallel to the r-axis), e.g., when the angle $\phi$ is about 45 degrees, as shown in FIG. 9. Note that for one embodiment, a ray 935 that is coincident with the z-axis, and thus coincident with the central axis of lens system 114 and thus bisects the angles $\gamma$, is reflected by about 90 degrees, e.g., when the angle $\phi$ is about 45 degrees, as shown in FIG. 9.

After radiation 910 is reflected from mirror 118, radiation 910 continues to converge by the angle $\gamma_6$ as it passes through filter 122, conduit 124, and aperture 128 until it reaches its focal point 940, as shown in FIG. 9. For one embodiment, radiation 910 converges to about a 1 millimeter by a 1 millimeter area at focal point 940. For another embodiment, the focal length of radiation source is the axial distance $z_{focal}$ from radiation emitter 130 to where the z-axis intersects mirror 118 plus the radial distance $r_{focal}$ from where the z-axis intersects mirror 118 to focal point 940, as shown in FIG. 9. For one embodiment, the just-defined focal length of radiation source about 3 inches.

Inserting filter 122 into compartment 126 (FIG. 3) aligns filter 122 with respect to mirror 118 so that substantially all of the radiation reflected from mirror 118 passes through filter 122, as shown in FIG. 9, with little or no additional adjustment. For one embodiment, inserting filter 122 into compartment 126 aligns filter 122 with respect to mirror 118 so that ray 935 is aligned with a central longitudinal axis of filter 122, as shown in FIG. 9, with little or no additional adjustment. Moreover, inserting conduit 124 into compartment 126 positions aperture 128 so that substantially all of the radiation reflected from mirror 118 passes through aperture 128, as shown in FIG. 9, with little or no additional adjustment. For one embodiment, inserting conduit 124 into compartment 126 positions aperture 128 so that the ray 935 is aligned with a central longitudinal axis of aperture 128, as shown in FIG. 9, with little or no additional adjustment.

For another embodiment, mirror 118 is a dichroic mirror that reflects ultraviolet radiation at a pre-selected nominal wavelength within about 5 nanometers of the nominal wavelength and passes longer wavelengths, as indicated by arrow 960 of FIG. 9, e.g., to a beam dump (not shown). For example, for embodiments where radiation emitter 130 is a semiconductor ultraviolet optical source, mirror 118 reflects wavelengths of the primary emission band of the semiconductor ultraviolet optical source in the ultraviolet region and passes the longer wavelengths of the secondary emission band of the semiconductor ultraviolet optical source, e.g., to the beam dump.

For one embodiment, at least the portion of wall 153 of housing 102 within compartment 120 (FIG. 3) that contains mirror 118 may be of a material that is transparent to the longer wavelengths (e.g., clear for wavelengths in the visible range) passed by mirror 118. This enables the longer wavelengths to exit housing 102 by passing through this portion of wall 153 within compartment 120, as indicated by arrow 975 in FIG. 2. The exiting longer wavelengths may then be directed to the beam dump.

For another embodiment, filter 122 may be a short-pass filter, such as a black-glass filter, gray filter, etc., that filters out any residual long-wave radiation that did not get passed by mirror 118.

Figure 10:
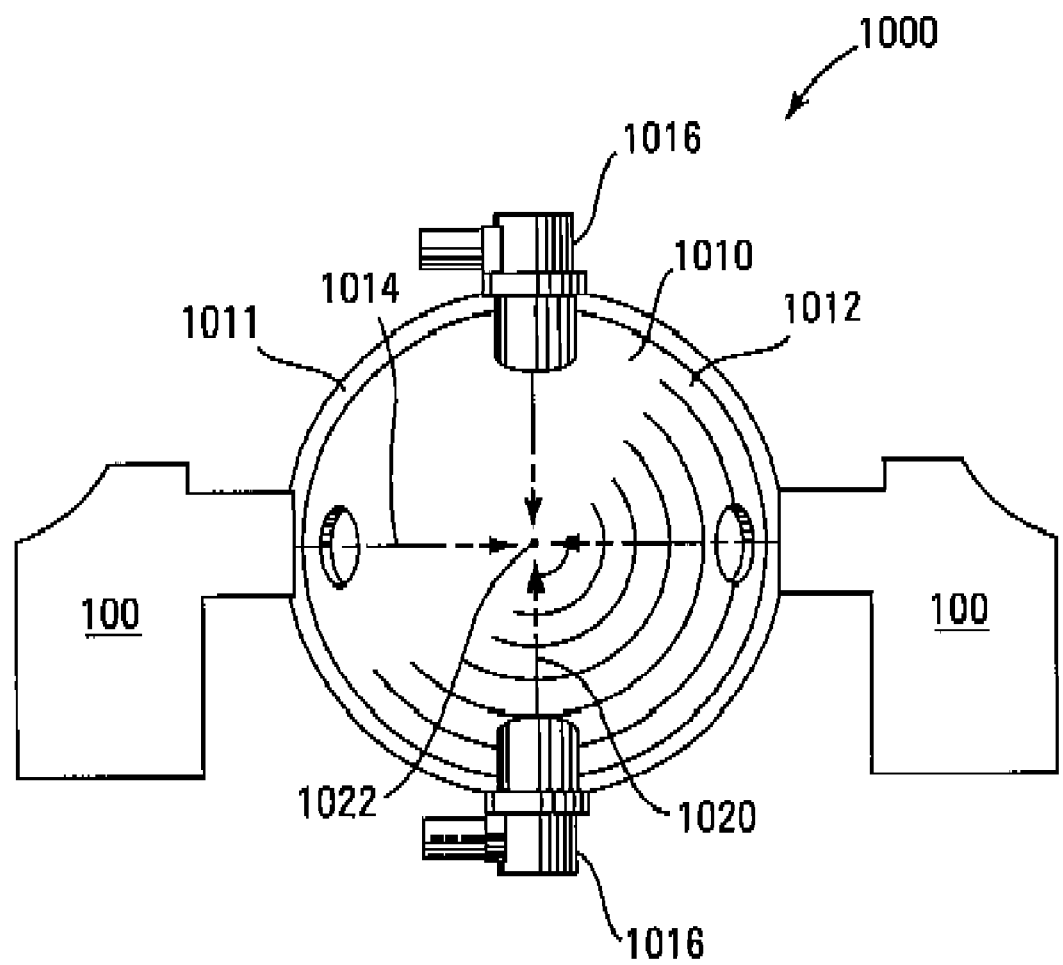
FIG. 10 is a schematic representation of an embodiment of a particle detector, according to another embodiment of the disclosure.

FIG. 10 is a schematic representation of a particle detector 1000, such as a biological aerosol detector, according to another embodiment. Detector 1000 has one or more radiation sources 100 in accordance with embodiments of the present disclosure.

Detector 1000 also includes an optical cavity 1010 in accordance with the embodiments of the particle (or biological aerosol) detectors described in U.S. Pat. No. 6,967,338 and U.S. patent application Ser. No. 11/268,758, both of which were incorporated by reference above. For one embodiment, optical cavity 1010 is formed in part by a shell 1011 for an elliptical mirror 1012. An aerosol sample drawn into optical cavity 1010 is excited by radiation that is provided by radiation source 100 that focuses this radiation onto the inner focal point of elliptical mirror 1012. For one embodiment, the inner focal point of elliptical mirror 1012 coincides with the focal point 940 of radiation source 100 (FIG. 9). The optical path from radiation source 100 to the inner focal point of elliptical mirror 1012 defines an excitation beam axis 1014.

As shown in FIG. 10, for one embodiment, detector 1000 includes first and second radiation sources 100 placed at opposite ends of excitation beam axis 1014. This configuration allows particles to be illuminated from two radiation sources 100, thereby providing twice the excitation power of devices that use a single excitation assembly. In addition, the wavelengths emitted by the first and second radiation sources 100 may be different, thereby allowing the detection of different biological aerosols or discrimination between detected aerosols.

The shell 1011 of elliptical mirror 1012 includes an inlet 1016 through which aerosol samples are drawn into the optical cavity formed by the housing. As described in U.S. Pat. No. 6,967,338, the biological aerosol detector shown in FIG. 10 utilizes an opposing intake flow design that defines an aerosol sampling axis 1020. The excitation beam axis 1014 is perpendicular to this aerosol sampling axis 1020, and both of these axes are perpendicular to a fluorescence detection axis 1022 that runs orthogonal to the top plan view of the detector 1000 that is shown in FIG. 10. A detector placed along fluorescence detection axis 1022 can detect the fluorescence radiation emitted by a biological molecule in the sampled aerosol that is excited by the ultraviolet radiation from the one or more radiation sources 100.

Embodiments of the disclosure provide a radiation source 100 that provides a collimated beam of radiation, e.g., ultraviolet radiation, at a focal point. For one embodiment, housing 102 of radiation source 100 has a plurality of compartments configured so that when their respective components are inserted therein, the components are optically aligned with respect to each other and are positioned at predetermined distances from each other, with little or no additional adjustment. This reduces the set up time required for positioning and aligning these components.

For example, inserting radiation-emitter assembly 110 in compartment 112 aligns its central longitudinal axis z" with the central longitudinal axis z of housing 102, as shown in FIGS. 2 and 6, with little or no additional adjustment. Inserting lens system 114 in compartment 116 sets the distance between radiation-emitter assembly 110 and lens system 114 to a predetermined distance and aligns the central longitudinal axis z' of lens system 114 with the central longitudinal axis z" of radiation-emitter assembly 110 and with the central longitudinal axis z of housing 102, as shown in FIGS. 2 and 6, with little or no additional adjustment. Inserting mirror 118 into compartment 120 sets mirror 118 at the predetermined angle ψ with respect to lens system 114 and sets the distance from lens system 114 to mirror 118 to a predetermined distance, as shown in FIG. 2, with little or no additional adjustment. Inserting filter 122 into compartment 126 aligns filter 122 with mirror 118 so that substantially all of the radiation reflected from mirror 118 passes through filter 122, as shown in FIG. 9, with little or no additional adjustment. Inserting filter 122 into compartment 126 (FIG. 3) aligns filter 122 with respect to mirror 118 so that substantially all of the radiation reflected from mirror 118 passes through filter 122, as shown in FIG. 9, with little or no additional adjustment. Inserting conduit 124 into compartment 126 positions aperture 128 so that substantially all of the radiation reflected from mirror 118 passes through aperture 128, as shown in FIG. 9, with little or no additional adjustment.

CONCLUSION

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A radiation source, comprising:
   a housing;
   a radiation-emitter assembly disposed, at least in part, in a first compartment of the housing;
   a lens system disposed in a second compartment of the housing so that the lens system is optically coupled to the a radiation-emitter assembly;
   a dichroic mirror disposed in a third compartment of the housing so that the mirror is optically coupled to the lens system; and
   a filter and a conduit disposed in a fourth compartment of the housing so that the filter and an aperture provided by the conduit are optically coupled to the mirror, wherein radiation exits the radiation source through the aperture.

2. The radiation source of claim 1, wherein the mirror is at an angle with respect to the lens system.

3. The radiation source of claim 1, wherein the mirror is at about a 45-degree angle with respect to the lens system.

4. The radiation source of claim 1, wherein a distance of the radiation-emitter assembly from an end of the housing is selectively adjustable.

5. The radiation source of claim 1, wherein radiation-emitter assembly comprises a radiation emitter that is attached to a substrate that is disposed between a base and a holder.

6. The radiation source of claim 5, wherein the base of the radiation-emitter assembly is disposed within the holder so that the substrate is disposed between an end of the base and an extension of the holder that extends inward toward a center of the holder.

7. The radiation source of claim 1, wherein the radiation-emitter assembly is selectively disposable within first and second pairs of slots formed in a wall the of housing within the first compartment for selectively adjusting a position of the radiation-emitter within the housing.

8. The radiation source of claim 1, wherein the radiation-emitter assembly comprises a semiconductor ultraviolet optical source.

9. The radiation source of claim 1, wherein the lens system comprises two or more lens elements connected in series.

10. The radiation source of claim 9, wherein each lens element comprises a lens surrounded by an integral flange that extends in an axial direction away from the radiation-emitter assembly.

11. The radiation source of claim 9, wherein each lens element comprises a lens having a first surface and a second surface, the first and second surfaces having different shapes.

12. The radiation source of claim 11, wherein the shape of the first surface is described by a first fourth-order curve and the shape of the second surface is described by an ellipse in combination with a second fourth-order curve.

13. The radiation source of claim 9, wherein the lens system is selectively comprises three lens elements connected in series.

14. The radiation source of claim 9, wherein the lens system comprises a spacer connected in series with two lens elements connected in series.

15. The radiation source of claim 14, wherein the spacer is disposed between the first compartment and the two lens elements connected in series.

16. The radiation source of claim 1, wherein the filter is a short-pass filter.

17. The radiation source of claim 16, wherein the short-pass filter is a gray filter or a black-glass filter.

18. The radiation source of claim 1, wherein the radiation source is part of a particle detector.

19. The radiation source of claim 18, wherein the radiation source focuses ultraviolet radiation onto a focal point within an optical cavity of the particle detector.

20. A radiation source, comprising:
    a housing;
    a radiation-emitter assembly disposed within the housing, wherein the radiation-emitter assembly is selectively positionable at first and second locations within the housing according to a nominal wavelength of radiation emitted by the radiation-emitter assembly;
    a lens system disposed within the housing so that the lens system is optically coupled to the a radiation-emitter assembly, wherein the lens system is selectively configurable between a first configuration corresponding to the first location of the radiation-emitter assembly and a second configuration corresponding to the second location of the radiation-emitter assembly;

a dichroic mirror disposed within the housing so that the dichroic mirror is optically coupled to the lens system, wherein the dichroic mirror forms an angle with respect to the lens system; and a filter and a conduit disposed in the housing so that the filter and an aperture provided by the conduit are optically coupled to the mirror, wherein the radiation exits the radiation source through the aperture.

21. The radiation source of claim 20, wherein the first configuration of the lens system comprises three lens elements connected in series and the second configuration of the lens system comprises a spacer connected in series with two lens elements connected in series so that a portion of the radiation-emitter assembly extends into the spacer.

22. A method of forming a radiation source, comprising:

forming a housing having first, second, third, and fourth compartments;

inserting at least a portion of a radiation-emitter assembly in the first compartment;

inserting a lens system in the second compartment, wherein inserting the lens system within the second compartment sets the lens system at a predetermined distance from the radiation-emitter assembly and aligns the lens system with the radiation-emitter assembly;

inserting a mirror in the third compartment, wherein inserting the mirror in the third compartment sets the mirror at a predetermined angle with respect to the lens system; and inserting a filter and a conduit in the fourth compartment, wherein inserting the filter and the conduit in the fourth compartment positions the filter and an aperture of the conduit through which the radiation exits the radiation source so that substantially all of the radiation reflected from the mirror passes through the filter and the aperture.

23. The method of claim 22 further comprises connecting two or more lens elements of the lens system in series, wherein connecting the two or more lens elements of the lens system in series sets a distance between lenses of successive lens elements to a predetermined distance and aligns the lenses of the successive lens elements with respect to each other.

* * * * *